(12) United States Patent
Powers et al.

(10) Patent No.: US 9,002,473 B2
(45) Date of Patent: Apr. 7, 2015

(54) ELECTRODE AND ENCLOSURE FOR CARDIAC MONITORING AND TREATMENT

(75) Inventors: Daniel J. Powers, Issaquah, WA (US); Shannon Fong, Seattle, WA (US); Eric Jonsen, Seattle, WA (US); Patrick Hauge, Bellevue, WA (US)

(73) Assignee: Koninklijke Philips N.V., Eindhoven (NL)

( * ) Notice: Subject to any disclaimer, the term of this patent is extended or adjusted under 35 U.S.C. 154(b) by 1603 days.

(21) Appl. No.: 11/577,370

(22) PCT Filed: Oct. 3, 2005

(86) PCT No.: PCT/IB2005/053245
§ 371 (c)(1),
(2), (4) Date: Apr. 17, 2007

(87) PCT Pub. No.: WO2006/046160
PCT Pub. Date: May 4, 2006

(65) Prior Publication Data
US 2008/0097546 A1    Apr. 24, 2008

Related U.S. Application Data

(60) Provisional application No. 60/623,196, filed on Oct. 29, 2004.

(51) Int. Cl.
*A61N 1/375* (2006.01)
*A61B 5/0424* (2006.01)
*A61N 1/04* (2006.01)

(52) U.S. Cl.
CPC ......... *A61B 5/0424* (2013.01); *A61B 2562/125* (2013.01); *A61N 1/046* (2013.01); *A61N 1/0472* (2013.01); *A61N 1/048* (2013.01); *A61N 1/0492* (2013.01)

(58) Field of Classification Search
USPC ........ 600/372, 391, 392, 547; 607/5, 36, 115, 607/142, 152, 27, 63, 149, 150, 153
See application file for complete search history.

(56) References Cited

U.S. PATENT DOCUMENTS

| | | | |
|---|---|---|---|
| 4,779,630 A | 10/1988 | Scharnberg et al. | |
| 4,979,517 A | 12/1990 | Grossman et al. | |
| 5,591,213 A * | 1/1997 | Morgan | 607/5 |
| 5,645,571 A * | 7/1997 | Olson et al. | 607/5 |
| 5,697,955 A * | 12/1997 | Stolte | 607/5 |
| 5,984,102 A | 11/1999 | Tay et al. | |
| 6,272,385 B1 * | 8/2001 | Bishay et al. | 607/142 |
| 6,694,193 B2 * | 2/2004 | Lyster et al. | 607/142 |
| 2001/0051821 A1 * | 12/2001 | Snyder | 607/142 |
| 2002/0082644 A1 * | 6/2002 | Picardo et al. | 607/1 |
| 2002/0082672 A1 | 6/2002 | Janae et al. | |
| 2003/0055478 A1 * | 3/2003 | Lyster et al. | 607/142 |
| 2003/0130714 A1 * | 7/2003 | Nielsen et al. | 607/142 |

FOREIGN PATENT DOCUMENTS

EP    0983775 A    3/2000

* cited by examiner

*Primary Examiner* — Carl H Layno
*Assistant Examiner* — Jennifer Ghand

(57) ABSTRACT

Defibrillator electrodes are sealed to the inside of a rigid enclosure. The enclosure is hinged to open and expose the electrodes for deployment. The electrode gel is sealed against moisture loss between the moisture impervious electrode backing and the inner surface of the enclosure. The enclosure may further include an electrical circuit for electrode self-testing, the circuit being broken when the enclosure is opened.

20 Claims, 6 Drawing Sheets

35, 36, 37, 38

ELECTRODE AND ENCLOSURE FOR CARDIAC MONITORING AND TREATMENT

The present invention relates in general to electrodes for medical instruments and, in particular, to medical electrodes and enclosures for cardiac monitors or defibrillation/pacing devices.

Sudden cardiac death is the leading cause of death in the United States. Most sudden cardiac death is caused by ventricular fibrillation ("VF"), in which the muscle fibers of the heart contract without coordination, thereby interrupting normal blood flow to the body. The only known treatment for VF is electrical defibrillation, in which an electrical pulse is applied to a patient's heart. The electrical shock clears the heart of the abnormal electrical activity (in a process called "defibrillation") by depolarizing a critical mass of myocardial cells to allow spontaneous organized myocardial depolarization to resume.

One way of providing electrical defibrillation is by automatic or semiautomatic external defibrillators, collectively referred to as "AEDs," which analyze ECG signals from the heart and, upon detection of a treatable arrhythmia, sends electrical pulses to a patient's heart through electrodes applied to the torso to defibrillate the patient or to provide for external pacing of the patient's heart. The use of AEDs by untrained or minimally trained operators for a patient in sudden cardiac arrest is a time critical operation. The electrical pulse must be delivered within a short time after onset of VF in order for the patient to have any reasonable chance of survival.

The reception of the patient's ECG signals and the application of the appropriate therapeutic pulses or currents is done through conductive pads or electrodes applied to the patient's torso and connected to the AED base unit. The AED is typically stored with electrodes that are sealed in an enclosure that protects the electrodes from contamination and retards desiccation. Before defibrillation can commence the operator must open the enclosure, remove the electrodes, and apply them to the patient. Electrodes that are sealed with a connector inside an enclosure, such as a bag, can require multiple steps by the operator. First, the operator must open the sealed bag. Second, the operator must plug the electrode connector into the AED base unit. Third, the operator must remove a release liner from one of the electrodes which typically covers a gel on the electrode pad and fourth, the operator must place the electrode on the patient. The operator must then repeat the third and fourth steps with the second electrode and place the second electrode on the patient.

The electrodes typically comprise a non-conductive base layer such as a plastic disc and a conductive layer that distributes the current transmitted to the electrode by the AED base unit. The non-conductive base layer is typically constructed of a thin, flexible polymeric material such as urethane foam, or a polyester or polyolefin laminate which is electrically insulating and provides structural integrity to the electrode. Conventionally, such electrodes further include a layer of adhesive material that is used to adhere the electrode to the patient's chest prior to and during delivery of the shocks. The adhesive material is typically a viscous water-based gel material that contains ionic compounds which increase the electrical conductivity of the material to provide a low resistance path for current to flow from the electrode to the patient's chest.

As is known in the art, electrodes used with automatic external defibrillators often are stored for relatively long periods of time until needed. During this time, the adhesive material can become desiccated. This desiccation decreases the effectiveness of the adhesive material in that it lowers the material's conductivity, which in turn raises the impedance at the contact area between the electrode and the skin. This increased impedance results in less current reaching the heart. Due to the problem of desiccation, the adhesive material normally is covered with a removable backing that reduces the material's exposure to air. Despite the provision of such backings, however, conventional adhesive materials still tend to dry out. For the purpose of preventing such desiccation, modern medical electrode packaging typically provides a sealed electrode storage environment and through-wall electrical connectivity to electrotherapy devices such as external defibrillators. The electrode packaging is typically either a flexible, heat-sealable laminate material, or a rigid, molded plastic material, both of which serve as a moisture barrier.

Flexible electrode housings such as foil-lined plastic bags provide economical and simple packaging for electrodes in many instances. Electrode wires may extend through the exteriors of known flexible housings, and connect directly to electrotherapy devices. A seal around the wires is typically achieved by heat-sealing the packaging material to the wires or by molding a plastic piece around the wires and sealing the packaging material to the piece. The electrodes themselves are typically arranged in the package so that they form an electrical circuit between themselves and the associated medical device. Prior art flexible housings, however, suffer from several drawbacks. Electrode function or sterility, for instance, may be compromised when electrode wiresets protrude through the flexible housing. Flexing may weaken the bond between the electrode wireset and the flexible material. In addition, the flexible material of the packaging may remain adhered to the electrode wires after placement of the electrodes on a patient, causing user confusion or delay.

Rigid structures offer an alternative to flexible housings, as exemplified by the electrode cartridge structure of the OnSite AED, manufactured by Philips Medical Systems of Andover, Mass., USA. Walls of rigid structures may include insert-molded electrical contacts, such as pins, which provide through-wall electrical connectivity between enclosed electrode wires and external electrotherapy devices. Thus, the electrode wires do not exit the cartridge, but rather, are permanently attached to electrical contacts that pass through the wall of the rigid structure. These electrical contacts complete the electrical connection to the intended device. Although rigid housing structures may sometimes be more expensive and have higher manufacturing costs than flexible housings, rigid structures are often selected because they have been designed to enclose electrode wiresets without compromising the seals of the structure, and they offer relatively simple user interfaces. Rigid structures, however, may be less desirable in certain situations such as at high altitudes in aircraft, when pressures inside the structures can greatly exceed ambient pressures. Also, heat-seal film, which is often stretched over rigid structure openings, may be vulnerable to puncture.

In addition to these disadvantages, these prior art electrode packaging materials, whether rigid or flexible, are external to the electrodes and must be disengaged from the electrodes prior to deployment of the electrodes. For instance, one form of prior art packaging comprises a flexible, heat-sealable pouch or envelope-style structure which must be torn and removed and the release liner or backing material adhered to the conductive gel stripped away in two separate steps. These are steps which reduce the efficiency of the device operator during a life-saving process such as cardiac defibrillation.

One form of electrode packaging which combines the benefits of both rigid and flexible enclosures is described in U.S. patent application Ser. No. 60/556,132, entitled "Self-storing medical electrodes and method for making same." In this design the two electrodes are heat sealed around their periphery to opposite sides of a rigid release liner. Such a package is simple to manufacture and easy to use. The conductive gel layers of each electrode is protected from desiccation by being sealed between the non-conductive base layer of the electrode and a side of the release liner. To use the electrodes each electrode is peeled away from its respective side of the release liner, which completely detaches the release liner from the electrodes and electrode wires. However it is undesirable to store the package in this form, as the exposed backs of the non-conductive base layers can become contaminated from the environment or perforated or damaged. Consequently it is generally desirable to store the package in a bag or other enclosure that will protect the electrodes from contamination or damage prior to use. There thus remains a need for an electrode storage system that is integrated within and is part of the electrode itself, that prevents desiccation of the electrically conductive gel materials contained therein, and that adequately protects the electrodes from contamination or damage. Additionally it may be desirable for the electrodes to be electrically interconnected for self-test purposes. Such a self-storing electrode would allow for long-term sealed storage and self-testing of the electrodes and ease of operation of the electrodes. In addition, such self-storing electrode would be useful in a wide array of applications for both receiving and transmitting current such as, for example, in cardiac defibrillation, pacing and monitoring. See also U.S. Pat. No. 6,694,193 (Lyster et al.) which also illustrates other approaches to electrode packaging.

In accordance with the principles of the present invention, an electrode and electrode enclosure are provided for an external defibrillator, pacing device or patient monitor. Two electrodes each comprise a conductive layer, a non-conductive backing, and an adhesive conductive gel layer. A rigid enclosure has two inside surfaces to which the electrodes are peripherally sealed, thereby sealing the gel layer between the non-conductive backing and the inside surfaces of the enclosure. Since the electrodes are sealed against the inside surfaces, there is no need for the enclosure to have an air-tight seal to prevent desiccation. This enables the electrode wires to pass freely through an aperture in the enclosure wall so that the electrode connector can be connected to the base instrument while the electrodes are stored in the enclosure. It also enables the enclosure to be shipped and used at high altitudes, as no pressure differential can develop between the inside and outside of the enclosure. It further enables the use of a simple closing means for the enclosure such as a latch, shrink-wrap or tape. No air-tight seal is required. When the electrodes are to be used the enclosure is opened and the electrodes are peeled off of the surfaces of the enclosure, leaving the electrodes completely free of the enclosure and out of the way of the patient and treatment provider.

In accordance with a further aspect of the present invention, the enclosure includes an electrical connection which electrically connects the stored electrodes for self-testing. In accordance with yet another aspect of the present invention, the electrical connection is electrically broken when the enclosure is opened. The opening of the electrical connection can be sensed by the base instrument, providing an indication that the electrodes are being applied and triggering an audible instruction for application; or an indicator which causes the base instrument to turn on; or an indication that someone has tampered with the electrodes.

In the drawings:

FIG. 1 provides a top view of one electrode body assembly usable in connection with embodiments of the present invention.

FIG. 2 provides an exploded perspective view of an electrode body assembly.

FIG. 3 provides a perspective view of a generally rigid electrode enclosure, before electrodes are attached, in the open configuration.

FIG. 4 provides a top view of a complete electrode assembly in accordance with an embodiment of the present invention.

Figure 1:
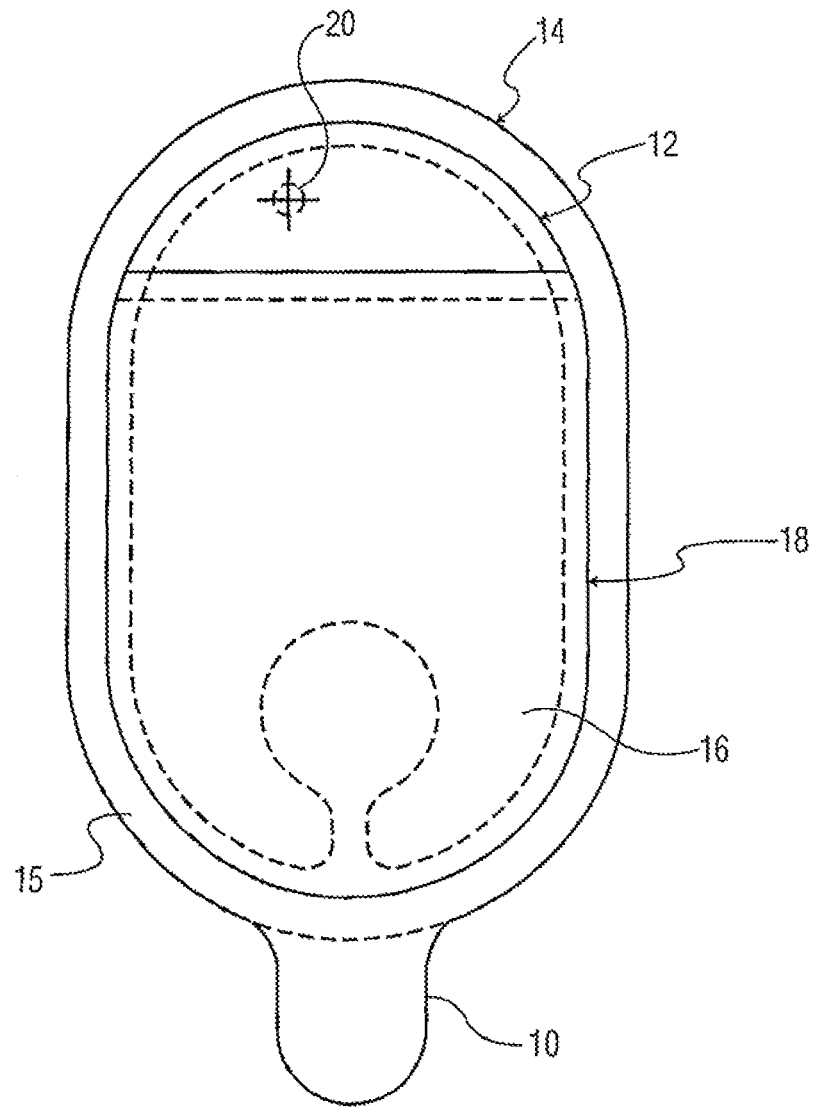

Turning now to the drawings, wherein like numerals designate like components, FIG. 1 illustrates a top plan view of a medical electrode 10 constructed in accordance with the principles of the present. The medical electrode 10 comprises an electrode body having a first and a second side, wherein the first side comprises a flexible barrier layer 14 comprising a heat-sealable material disposed at least about its periphery 15 and the second side comprises a conductive layer 16. The medical electrode 10 further comprises an electrically conductive gel layer 18 disposed on the electrode body 10 and which is in electrical communication with the conductive layer 16. A hole 20 for a rivet allows for attachment of an electrode wire (not shown in this view) to the electrode 10. A rivet cover 12 overlies the rivet hole to prevent direct electrical contact between a patient and electrode wire connectors when the electrode 10 is affixed to the patient. Rivet cover 12 also lies over a portion of the conductive layer 16 and extends underneath a portion of the conductive gel layer 18.

Figure 2:
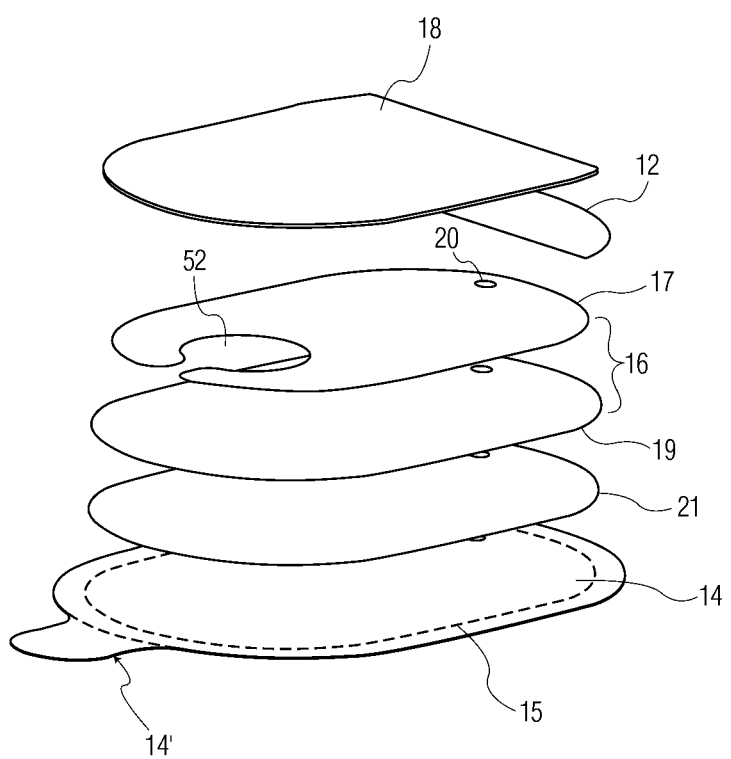

As shown in FIG. 2, flexible barrier layer 14 overlies and is coupled to conductive layer 16, which in turn is disposed over gel layer 18. Gel layer 18 is concentric with and within the edge of the flexible barrier layer 14 in order to establish the heat sealing periphery 15 around the outer edge of gel layer 18. The flexible barrier layer 14 has an extension 14' which extends from its periphery and serves as a pull tab when peeling the electrode away from its stored condition discussed below. In the illustrated embodiment, conductive layer 16 is comprised of a tin layer 17 laminated over a reinforcement layer 19 of polymeric material. Reinforcement layer 19 is attached by adhesive 21 or other attachment means to flexible barrier layer 14. Tin layer 17 is shaped with a void area 52, opposite the rivet hole 20, which is used for electrode self-test purposes as discussed below.

Heat-sealable material 15 may for example comprise a thermoplastic polymeric material. As used herein, a "heat-sealable" or "heat seal coated" material refers to a substrate that readily forms a seal between itself and another surface of a like or different substrate with the application of heat. Some heat-sealable or heat seal coated materials are also effective as vapor, moisture or air barriers. Typically, the heat-sealable material comprises a thermoplastic polymeric material. A variety of heat-sealable and heat seal coated materials are commercially available, and are within the scope of the present invention. For example, in some embodiments the heat-sealable material comprises films of polyethylene, spun-bonded polyolefin (TYVEK®, DuPont, Wilmington, Del.), polyvinyl chloride, ionomer resin, polyamides, polyester, polypropylene, polycarbonate, or polystyrene. A heat-sealable flexible laminate material suitable for use with the present invention is commercially available from Cadillac Products, Inc. in Troy, Mich.

As would be appreciated by those skilled in the art, the heat-sealable flexible material could alternatively be comprised of two layers comprising flexible barrier layer 14 under a separate heat-sealing layer 15. The layers may also be arranged in a different order. Thus, in one embodiment, the flexible barrier layer 14 further comprises a vapor or oxygen/air barrier material comprising a polymeric film or sheet, a foil material, or a coated substrate comprising a metal, textile, paper, or non-woven material coated with a polymeric material. Some exemplary vapor or air barrier materials preferably comprise a laminate such as a metallized polyester that has been laminated to low-density polyethylene (MPPE). In another embodiment, the vapor or air barrier comprises a fluoropolymer film such as polychlorotrifluoroethylene (e.g., ACLAR®, Honeywell, Inc.).

As will also be appreciated by those skilled in the art, the conductive layer 16 may comprise any of a number of prior art means for transferring current or voltage to the gel layer 18. Specific examples include thin layer strips of a conductive material such as a metal sheet or foil, or a laminate composition comprising a metal such as tin foil and a polymeric or other substrate material to provide physical support such as polyester.

In other embodiments, the conductive layer 16 may comprise a conductive ink that is printable on a substrate surface. For example, the conductive layer 16 may comprise a silver and carbon/graphite-based ink and any number of resins that are applied to the surface of a printable surface such as polyvinylchloride, polypropylene or other polymer substrate.

The gel layer 18 may comprise any number of widely available conductive compounds that maintain direct electrical contact with the skin and permit continued contoured adhesion to the body of a patient. The gel layer 18 may preferably also possess a pressure sensitive quality to promote adhesion to the body of a patient.

Figure 3:
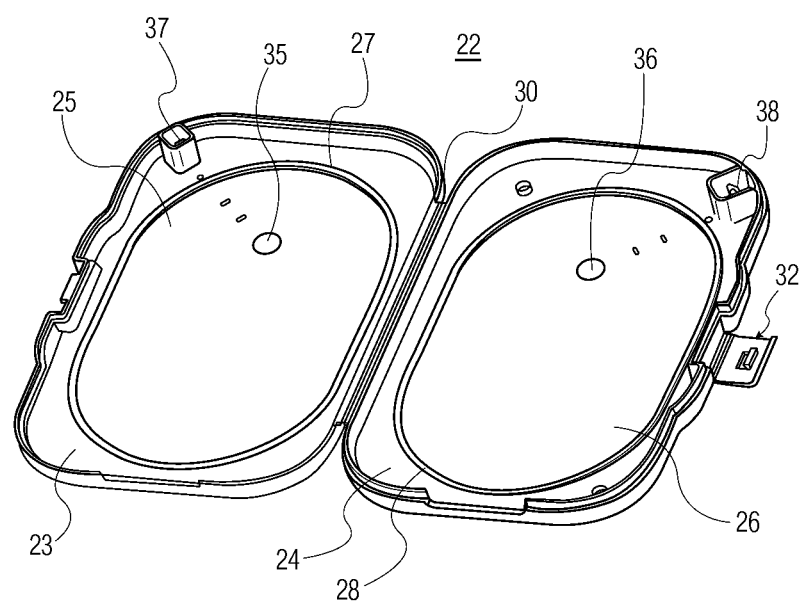

Referring now to FIG. 3, an electrode enclosure 22 is shown. Enclosure 22 is shown in the open position, displaying two halves 23 and 24, each side having an electrode release surface 25 and 26. The enclosure halves 23 and 24 are joined with a living hinge 30 formed during the molding of enclosure 22, although any suitable hinge may be used. Alternatively, the enclosure halves 23 and 24 could be held closed and opened without using any hinge structure at all.

Enclosure 22 in this embodiment is closed about the hinge 30 and held in the closed position by a latch or clasp 32, which in this embodiment is also formed during the molding process. In this embodiment, clasp 32 and hinge 30 are formed integral to the enclosure 22, but the invention is not so limited. An embodiment of the present invention may comprise an enclosure with no hinge or clasp which is held closed by some other means such as tape, or by interlocking edges which snap together.

The release surfaces 25 and 26 are shaped to enclose the electrically conductive gel layer 18 of each electrode 10, and in this embodiment sealing is promoted by surrounding the surfaces with raised edges 27 and 28. The raised edges 27 and 28 serve to contain the gel layer 18 and also as a heat sealing surface to bond to the sealable periphery 15 of each electrode 10.

As will be appreciated by those skilled in the art, a wide variety of substrates may be utilized as an enclosure 22 in the practice of the present invention. Typically, such enclosure 22 material is chosen such that the electrically conductive gel layer 18 of the electrode 10 will readily peel away from the electrode release surface 25,26 while remaining attached to the electrode 10. In some preferred embodiments, the enclosure 22 comprises a polymeric sheet such as high-density polyethylene, a coated paperboard, or foam, such that the non-conductive release surface provides a relatively rigid surface with respect to the flexible electrode 10 which is peeled away from the release surface just prior to use. Enclosure 22 should further resist moisture transmission through the enclosure material.

In other embodiments enclosure 22 comprises a material treated with an adhesion-reducing agent such as a surface-treated polymeric sheet. For example, enclosure 22 may comprise silicon-treated polyethylene, polypropylene, polyester, acrylate, polycarbonate, or wax or plastic coated paperboard or foam. An adhesion-reducing agent as used herein refers to an agent that, when applied to a substrate, reduces the coefficient of friction of that substrate. In other embodiments, depending on the choice of heat-sealable material 15 that is chosen, enclosure 22 may comprise an uncoated or non-surface treated substrate from which the heat-sealable material 15 will readily peel off. In other embodiments, at least a portion of the electrode release surfaces 25, 26 of enclosure 22 that come into contact with the electrically conductive gel layer of the electrode is coated with an adhesion-reducing material such that the gel separates cleanly from the backing. Other portions of enclosure 22 that are sealed directly to heat-sealable material 15 are left uncoated since it is desired that a strong seal be maintained between the raised edges 27,28 and the heat-sealable material 15 during extended storage of the electrodes 10.

In accordance with a further aspect of the present invention enclosure 22 may further comprise conductive elements 35, 36 disposed on release surfaces 25, 26.

Conductive elements 35, 36 provide a conductive surface within the release areas and a conductive path from each surface to a connector 37, 38 at the periphery of enclosure 22. The respective connectors on conductive elements 35, 36 mate when enclosure 22 is closed, thus providing a conductive path from release surface 25 to release surface 26. As discussed below, this conductive path enables electrode self-test, and provides an indication to the defibrillator or other that enclosure 22 has been opened.

Figure 6:
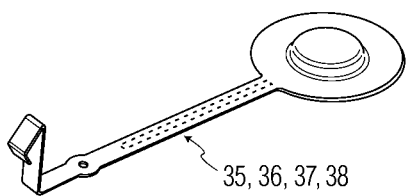
FIG. 6 is a perspective view of the electrical conductive element disposed within each half of the rigid electrode enclosure according to one embodiment of the invention.

In a preferred embodiment, conductive elements 35, 36 are molded into enclosure 22. However, conductive elements 35, 36 can alternatively be disposed on the interior or exterior surface of enclosure 22, or can comprise a single conductive member extending from one release surface to the other. FIG. 6 illustrates a conductive element 35,37 or 36,38 prior to assembly with enclosure 22.

Enclosure 22 can alternatively be disposed with an interior surface for storing a single electrode, or with interior surfaces for storing three or more electrodes. The optional conductive element 35 in the single electrode enclosure 22 embodiment would be disposed in direct electrical communication with a defibrillator device for self test purposes. The optional conductive elements 35,36 for each of the plurality of electrodes could be disposed in any number of arrangements with each other and with the defibrillator device as suitable for self-test purposes.

Figure 4:
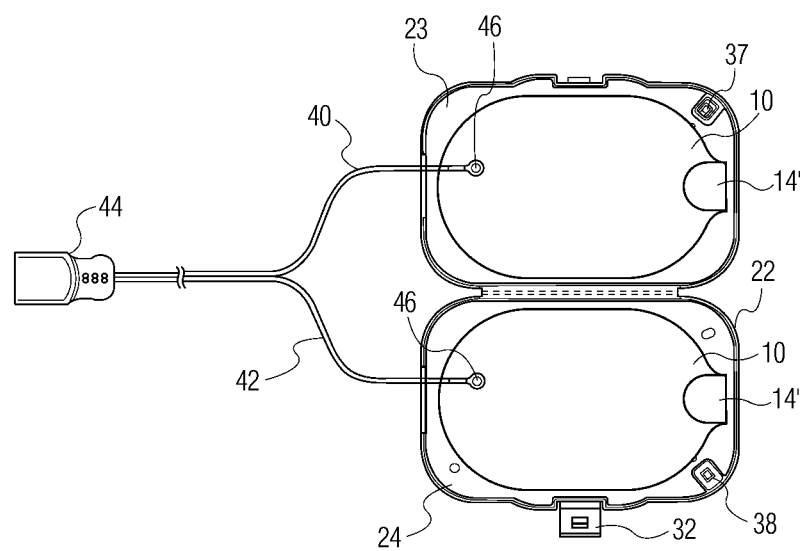

FIG. 4 illustrates an embodiment of the present invention with two electrodes 10 sealed in enclosure 22, with enclosure 22 in the open position. The pull tabs 14' are folded down to be inside the enclosure when the two enclosure halves are closed. In this illustration the lead wires 40, 42 are attached to the respective electrodes 10 by rivets 46. The opposite ends of lead wires 40, 42 are attached to a two pin connector 44, one pin for each lead wire, which in turn plugs into the base instrument with which the electrodes are used, such as a defibrillator, pacer, or monitoring instrument.

Figure 5:
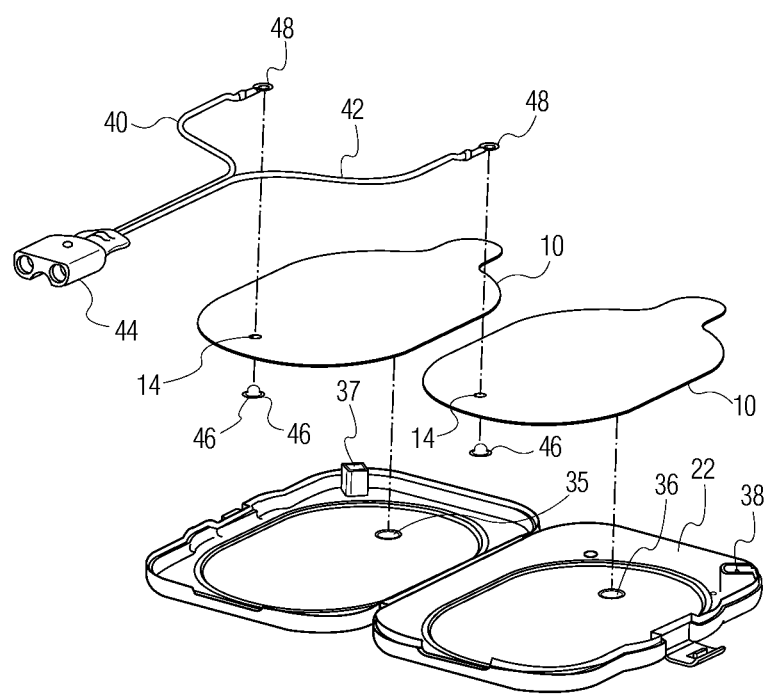
FIG. 5 is an exploded perspective view of a complete electrode assembly in accordance with an embodiment of the present invention.

FIG. 5 is an exploded view of the FIG. 4 embodiment, showing one means of attachment for lead wires 40, 42 to respective electrodes 10. Each lead wire 40, 42 is attached to a respective electrode 10 using a rivet 46, the flange 46' of which overlays and is in electrical contact with conductive layer 16. Conductive layer 16, not visible in this view, is on the adhesive gel side of electrode 10. The shaft of rivet 46 extends through the electrode 10. A washer-type connector 48 on the ends of lead wires 40,42 is disposed on the rivet 46 shaft. Preferably, the assembly of rivet 46 and connector 48 is disposed on electrode 10 such that flexible barrier layer 14 is compressed between the connector 48 and the rivet flange 46', resulting in an air-tight, form-fitting seal around the rivet hole in flexible barrier layer 14. Rivet flange 46' forms a generally hermetic seal around the periphery of the rivet hole with conductive layer 16.

As would be appreciated by one of skill in the art, the lead wire 40, 42 can be electrically connected to respective electrode 10 by connector 48 or by other connecting means, including but not limited to a ring tung terminal, staple, grommet, screw, bolt, or a pin connector or other electrically conducting fastening means which is capable of enabling electrical signals to traverse the flexible barrier layer 14 to conductive layer 16. Connector 48 can be disposed such that the lead wire 40 or 42 passes around or through the sealing seam formed by flexible barrier layer 14 and enclosure 22.

FIG. 5 also illustrates the disposition of the electrodes 10 over the conductive elements 35, 36. When the electrodes are sealed in place in the enclosure, respective conductive layers 16 are in electrical communication with conductive elements 35, 36 via electrically conductive gel layers 18 on the undersides of the electrodes. A preferred disposition of conductive layer 16 relative to gel layer 18 and conductive element 36 is described in U.S. Pat. No. 6,694,193 entitled "Medical Electrode and Release Liner Configurations Facilitating Packaged Electrode Characterization", hereby incorporated by reference. When enclosure 22 is closed, mating connectors 37 and 38, a circuit is formed from one pin of connector 44, through a lead wire 40, a connector 48, a rivet 46, conductive layer 16, electrically conductive gel 18, conductive element 35,37, conductive element 38,36, electrically conductive gel 18, conductive layer 16 a rivet 46 on the other electrode, a connector 48, and through lead wire 42 to the other pin of connector 44. The described circuit is useful for performing self-tests on the electrodes during storage, and for determining whether the electrodes 10 have been deployed during a rescue or the enclosure opened. As long as the enclosure is closed and the connector 44 plugged into a base instrument, the base instrument will see the impedance of the electrode and enclosure circuit just described. As soon as the enclosure is opened the base instrument will see an infinite impedance, alerting the instrument that use of the electrodes is imminent or that someone has tampered with the case. The base instrument can differentiate between the opening of the case and the unplugging of the connector 44 by sensing that the connector remains plugged in with an optical, mechanical, or electromagnetic sensor in or adjacent to the socket into which connector 44 plugs.

The advantages of the present invention become apparent when used with a medical device such as a defibrillator. In one embodiment, the use of a common enclosure 22 for both electrodes provides a convenient means of maintaining electrical contact between them, whether by the conductive elements 35, 36 as shown in FIG. 5, or by any other means known in the prior art, including a single conductive strip extending from the conductive layer 16 of one electrode 10 to another, or separate conductive strips extending from the conductive layer and meeting at the periphery of the enclosure 22, such that electrical communication between the electrodes 10 is maintained. Electrical communication between electrodes 10 is broken when enclosure 22 is opened, or when connector 44 is removed from the medical device. The former one of these states indicates to the medical device that an operating state has been entered, wherein the medical device can automatically react accordingly. Further, a quality of electrical communication between electrodes 10 may change as electrically conductive gel layer 18 ages, such as a change in the impedance through the self-test circuit path described above, indicating to the medical device that the electrodes 10 may no longer be usable.

In the case where the base instrument performs defibrillation such as a pacer/defibrillator, it is generally desirable that any electrical charge carried from a defibrillator to the patient through the lead wires occurs in a controlled manner during defibrillation and not while the operator is carrying out preparatory steps prior to deployment. To protect the operator in such situations, the rivet cover 12 may be provided. Removal of the electrode 10 from enclosure 22 otherwise would expose the rivet 46. In order to protect the operator from physical contact with the connector 48 and rivet 46 which are electrically connected to the electrical source, the electrode further comprises rivet cover 12 interposed between a portion of conductive layer 16 and enclosure 22 such as rivet cover 12 shown in FIG. 2.

Figure 7:
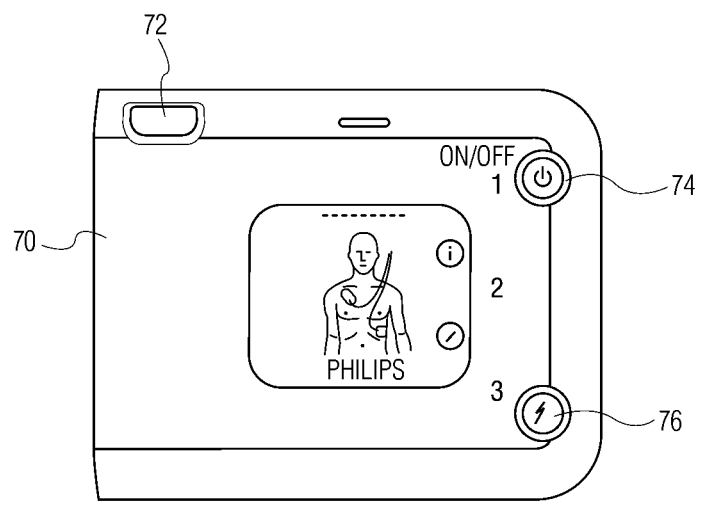
FIG. 7 illustrates an AED base instrument which is operable with the electrodes of the present invention.

FIG. 7 illustrates an AED base unit 70 suitable for use with enclosed electrodes of the present invention. The AED has several controls including an on/off button 74 by which the AED is turned on by an operator, and a shock button 76. The AED 70 has a socket 72 into which the electrode connector 44 is plugged. The socket 72 includes a sensor as described above which detects when a connector is or is not plugged into the socket. Preferably a set of electrodes is plugged into the socket 72 while the AED is stored for use so that the AED can periodically perform a self-test of the conductive adhesive gel of the electrodes as described above. Should the impedance of the test circuit change to an undesired state, the AED 70 alerts an attendant by an audible, visual, or electromagnetic (e.g., radio) warning. In the case where the connector 44 remains plugged in and the circuit impedance become infinite, the AED 70 senses that the electrodes are about to be deployed for a defibrillation. The AED 70, if not previously turned on, could then respond by powering itself in readiness for a rescue. The AED may also respond with a series of audible prompts, instructing the operator in correct placement of the electrodes on the patient as depicted on the front of AED 70. However, if an extended period of time passes after the impedance has changed (and remained infinite or reverted to the low impedance state) with no operator interaction, the AED may conclude that there has been tampering with the electrode enclosure or that some other fault condition has occurred. In such case the AED unit may issue an audible, visual or electromagnetic warning that attention is required. After a rescue has been performed by an on-site responder and a medical professional arrives with his or her own defibrillator or monitor, the connector 44 can be unplugged from the AED 70 and plugged into the unit of the medical professional for continued patient monitoring and/or treatment.

An embodiment of the present invention can provide numerous benefits. The hard enclosure protects the electrodes from damage. With the electrodes sealed to the inside of the enclosure to retard desiccation, there is no need for an airtight seal of the enclosure opening. This means that the inside pressure will be the same as ambient pressure, promoting use of the invention in airplanes and other high altitude situations. When the enclosure is opened and the electrodes peeled away, the enclosure is completely free of the electrodes and their leads and can be set aside away from the rescuer and patient.

Other modifications to the described embodiments will readily occur to those skilled in the art. For instance, it may not be necessary to have a raised sealing lip 27,28. It may be simpler and just as effective to seal the electrodes to flush surfaces inside the enclosure. Other sealing means such as adhesives may also or alternatively be used. Compression sealing may be used in some embodiments. For example, an electrode may be laid with its sealing periphery in contact with a gasket in the shape of the sealing periphery, a compression ring laid over the outside of the sealing periphery, the second electrode laid gel side up on the compression ring, and a second gasket laid over the sealing periphery of the second electrode. When the enclosure is closed and latched, the gel surfaces are sealed against the release surfaces 25,26 by the compression ring and gaskets. The conductive elements 35, 36 may be electrically connected by a conductor inside the enclosure which is not broken when the enclosure is opened. Alternatively, the elements 35,36 may extend through the wall of the enclosure and be interconnected by a thin conductive layer taped on the outside of the enclosure from one conductive element to the other across the opening between the two enclosure halves. The tape may serve to keep the enclosure closed prior to use, and opening the enclosure would necessitate breaking or disconnecting the taped conductive layer, alerting the AED that the enclosure has been opened for deployment of the electrodes. The electrodes can be produced and sealed in place without the leads connected to them, with the leads being attached after the enclosure has been opened for use of the electrodes.

What is claimed is:

1. An electrode and enclosure for a medical monitoring or therapy instrument comprising:
    an enclosure formed of a substantially rigid, moisture impervious material and having an inner surface against which one or more electrodes may be sealed, the enclosure having an open state in which electrodes inside the enclosure may be accessed and a closed state;
    first and second electrodes each having a substantially moisture-impervious outer layer, an electrically conductive gel layer, the outer layer of each electrode being peripherally sealed to the inner surface of the enclosure prior to use;
    an electrical circuit disposed on the enclosure comprising first and second mateable connectors which are in electrical contact with the gel layer of each electrode when the electrodes are sealed to the inner surface of the enclosure, the mateable connectors being open when the enclosure is in its open state and the mateable connectors being mated when the enclosure is in its closed state to electrically connect the gel layers of the electrodes; and
    a closing device which retains the enclosure in its closed state prior to use of the electrodes,
    wherein the electrode further comprises a metallic layer located between the outer layer and the gel layer.

2. The electrode and enclosure of claim 1, wherein the gel layer further comprises an adhesive conductive gel.

3. The electrode and enclosure of claim 1, wherein the outer layer further comprises a main body with a tab extending from the main body of the outer layer by which the electrode may be peeled away from its sealed location.

4. The electrode and enclosure of claim 1, wherein the enclosure comprises a molded polymer.

5. The electrode and enclosure of claim 1, wherein the enclosure further comprises first and second halves, each having an electrode release surface,
    wherein an electrode is sealed to each of the release surfaces.

6. The electrode and enclosure of claim 5, wherein the release surfaces further include a raised edge which aligns with the periphery of the outer layer of an electrode.

7. The electrode and enclosure of claim 5, wherein each release surface further includes a conductive element, the two conductive elements being elements of the electrical circuit which are electrically connected when the enclosure is closed.

8. The electrode and enclosure of claim 7, wherein the electrical connection between the two conductive elements is broken when the enclosure is opened.

9. The electrode and enclosure of claim 7, wherein each electrode further includes a lead electrically connected to the gel layer; and further comprising
    an automatic external defibrillator (AED) having an electrode test circuit connected to the electrode leads.

10. The electrode and enclosure of claim 9, wherein the electrical connection between the two conductive elements is broken when the enclosure is opened,
    wherein the breaking of the electrical connection is sensed by the AED.

11. The electrode and enclosure of claim 5, wherein the first and second halves are joined by a hinge; and
    wherein the closing device comprises a latch.

12. The electrode and enclosure of claim 11, wherein the enclosure halves are formed of a molded polymer,
    wherein the hinge and latch are integral to the enclosure halves and formed during the molding of the enclosure halves.

13. The electrode and enclosure of claim 12, wherein the electrodes each include an electrical lead attached to the electrode and each of the electrical leads are attached to a two pin connector,
    wherein the two pin connector and the electrical leads extend from the enclosure when the enclosure is closed.

14. The electrode and enclosure of claim 13, further comprising an automatic external defibrillator (AED),
    wherein the two pin connector is connected to the AED while the enclosure is closed prior to use of the electrodes.

15. The electrode and enclosure of claim 1, wherein the closing device comprises a latch.

16. The electrode and enclosure of claim 1, wherein the closing device comprises a polymeric material.

17. The electrode and enclosure of claim 16, wherein the closing device comprises tape.

18. The electrode and enclosure of claim 17, wherein the closing device comprises shrink wrap.

19. An enclosure for a pair of electrodes for use in a defibrillator comprising:
    a hinged enclosure, having an open state and a closed state, formed of a substantially rigid, moisture impervious material;
    first and second release surfaces formed on an inner surface of the hinged enclosure;
    first and second heat sealing surfaces disposed on an inner surface of the hinged enclosure and about the periphery of the first and second release surfaces;
    first and second conductive elements disposed on the first and second release surfaces;

first and second mateable connector ends disposed on the enclosure in conductive contact with first and second conductive elements, the mateable connector ends being mated when the enclosure is in the closed state; and a closing device which retains the enclosure in the closed state.

20. The enclosure of claim 19, further comprising:

first and second electrodes each comprising
- a substantially moisture-impervious outer layer with a heat sealing periphery sealed to the respective first and second heat sealing surfaces on the enclosure,
- an electrically conductive gel layer disposed concentric with and within the edge of the outer layer heat sealing periphery and further disposed in conductive contact with the respective first and second conductive elements, and
- an electrode wire conductively coupled to the gel layer, wherein an electrical circuit including a conductive path through each gel layer is formed when the enclosure is in the closed state.

* * * * *